US008853354B2

(12) United States Patent
Baba et al.

(10) Patent No.: US 8,853,354 B2
(45) Date of Patent: Oct. 7, 2014

(54) POLYION COMPLEX COMPRISING HYDROPHOBIZED POLYAMINO ACID AND USE OF THE SAME

(75) Inventors: Masanori Baba, Kagoshima (JP); Tomofumi Uto, Kagoshima (JP); Mitsuru Akashi, Suita (JP); Takami Akagi, Minoh (JP); Chikateru Nozaki, Kikuchi (JP); Kazuyoshi Kaminaka, Kikuchi (JP)

(73) Assignee: Kagoshima University, Kagoshima (JP)

( * ) Notice: Subject to any disclaimer, the term of this patent is extended or adjusted under 35 U.S.C. 154(b) by 450 days.

(21) Appl. No.: 13/258,867

(22) PCT Filed: Mar. 26, 2010

(86) PCT No.: PCT/JP2010/055463
§ 371 (c)(1),
(2), (4) Date: Nov. 2, 2011

(87) PCT Pub. No.: WO2010/110445
PCT Pub. Date: Sep. 30, 2010

(65) Prior Publication Data
US 2012/0095186 A1 Apr. 19, 2012

(30) Foreign Application Priority Data
Mar. 27, 2009 (JP) .................................. 2009-079712

(51) Int. Cl.
C07K 2/00 (2006.01)
C07K 14/005 (2006.01)
B32B 5/16 (2006.01)
C07K 14/77 (2006.01)
A61K 47/48 (2006.01)
C07K 14/00 (2006.01)
C08G 69/10 (2006.01)
C07K 7/02 (2006.01)
C08G 69/48 (2006.01)

(52) U.S. Cl.
CPC ........... C07K 14/00 (2013.01); A61K 47/48315 (2013.01); A61K 47/48884 (2013.01); C08G 69/10 (2013.01); C07K 7/02 (2013.01); C08G 69/48 (2013.01)
USPC ............ 530/300; 530/367; 530/395; 428/402

(58) Field of Classification Search
None
See application file for complete search history.

(56) References Cited

U.S. PATENT DOCUMENTS

| 5,700,459 | A | 12/1997 | Krone et al. | |
|---|---|---|---|---|
| 6,022,860 | A | 2/2000 | Engel et al. | |
| 2001/0024829 | A1* | 9/2001 | Wolff et al. | 435/455 |
| 2006/0110356 | A1 | 5/2006 | Kataoka et al. | |
| 2009/0047517 | A1 | 2/2009 | Caruso et al. | |

FOREIGN PATENT DOCUMENTS

| EP | 1 872 793 | 1/2008 |
|---|---|---|
| JP | 4-225915 | 8/1992 |
| JP | 2001-520662 | 10/2001 |
| JP | 2005-8614 | 1/2005 |
| JP | 2008-285624 | 11/2008 |
| WO | 2006/112477 | 10/2006 |
| WO | 2008/041703 | 4/2008 |

OTHER PUBLICATIONS

Okamoto et al. (Vaccine. 2007; 25: 8270-8278).*
T. Akagi et al., "Protein Direct Delivery to Dendritic Cells using Nanoparticles based on Amphiphilic Poly(Amino Acid) Derivatives", Biomaterials, vol. 28, pp. 3427-3436, 2007.
Supplementary European Search Report issued Jun. 12, 2013 in EP Application No. 10756251.4.
Supplementary European Search Report issued May 17, 2013 in European Application No. 10756251.4.
M. Satoh et al., "Helix Formation of Poly(L-Glutamic Acid) and Poly(L-Lysine) in the Polyion Complex Prepared in Aqueous Alcohol Solutions", Polymer, vol. 35, No. 16, pp. 3492-3498, Aug. 1, 1994.
M. Kunioka et al., "Preparation Conditions and Swelling Equilibria of Biodegradable Hydrogels Prepared from Microbial Poly(γ-Glutamic Acid) and Poly(ε-Lysine)", Journal of Environmental Polyer Degradation, vol. 4, No. 2, pp. 123-129, Apr. 1, 1996.
T. Akagi et al., "Stabilization of Polyion Complex Nanoparticles Composed of Poly(Amino Acid) Using Hydrophobic Interactions", Langmuir, vol. 26, No. 4, pp. 2406-2413, Feb. 16, 2010.
International Search Report issued Jun. 29, 2010 in International (PCT) Application No. PCT/JP2010/055463.
English translation of the International Preliminary Report on Patentability in corresponding Application No. PCT/JP2010/055463.

(Continued)

Primary Examiner — Shanon A Foley
(74) Attorney, Agent, or Firm — Wenderoth, Lind & Ponack, L.L.P.

(57) ABSTRACT

A polyion complex (PIC) or a PIC nanoparticle that may be easily prepared, and that is finally disappeared in vivo due to its suitable biodegradability while exhibiting high stability in vivo, an immunotherapy agent comprising the PIC nanoparticle to which various antigen proteins or peptides may be easily conjugated or incorporated and/or which may be easily mixed with the antigen proteins or peptides, as well as a process for preparing thereof are provided. Specifically, a polyion complex (PIC) comprising a hydrophobized poly (acidic amino acid) and a basic polypeptide, a nanoparticle thereof having a particle shape, an immunotherapy agent comprising the PIC nanoparticle, as well as a process for preparing the PIC, comprising steps of introducing a hydrophobic amino acid to a poly(acidic amino acid) to prepare a hydrophobized poly(acidic amino acid), and dissolving the hydrophobized poly(acidic amino acid) prepared to a buffer, and it is mixed with a basic polypeptide dissolved in a buffer.

21 Claims, 19 Drawing Sheets

(56) References Cited

OTHER PUBLICATIONS

Office Action dated Sep. 13, 2012 in corresponding Chinese Application No. 201080014140.4.

English translation of Office Action issued Mar. 27, 2009 in corresponding Japanese Application No. 2009-079712.

* cited by examiner

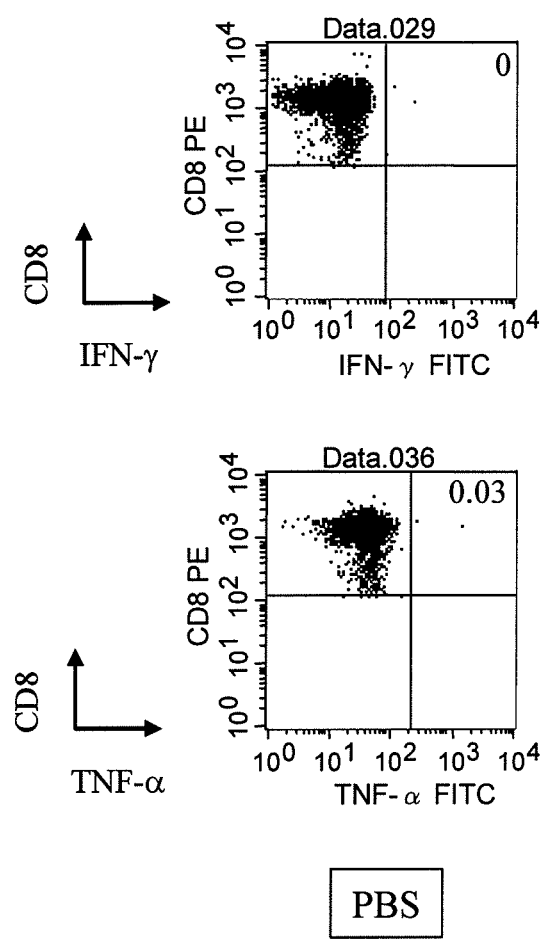

OVA-PIC NP

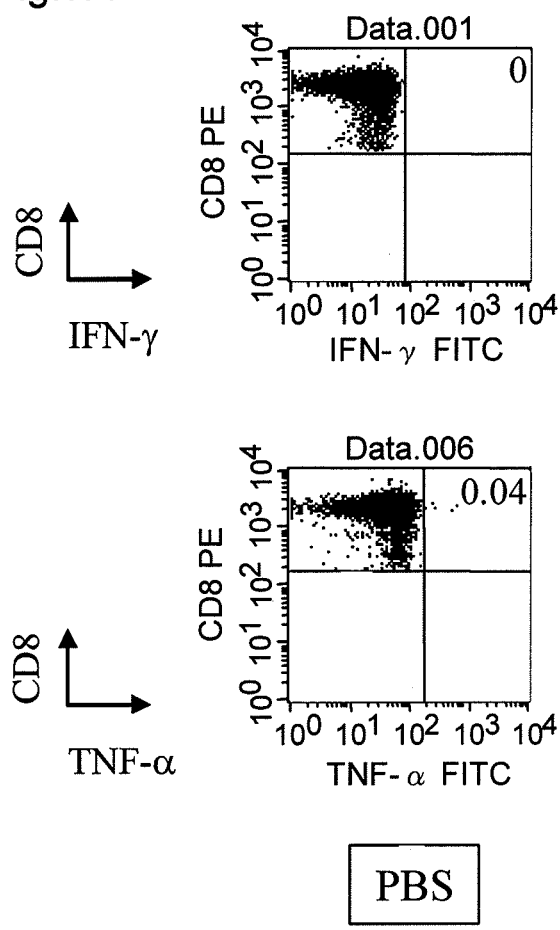

Fig. 7B
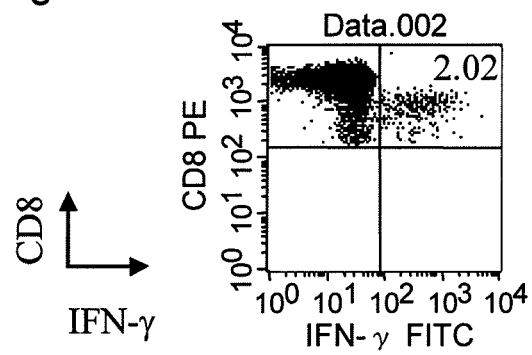
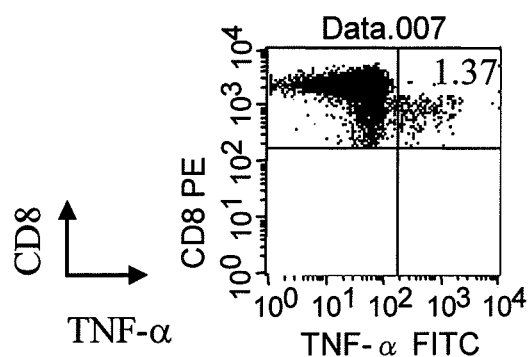
OVA-PIC NP
ε-PL 1/1

Fig.7C
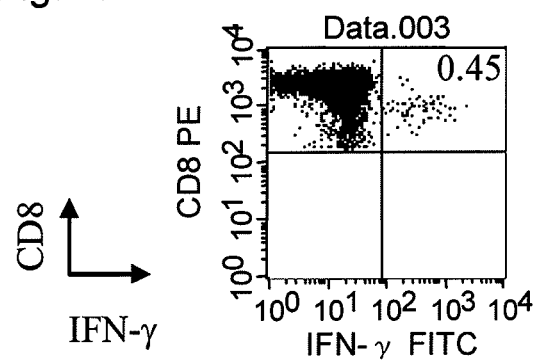
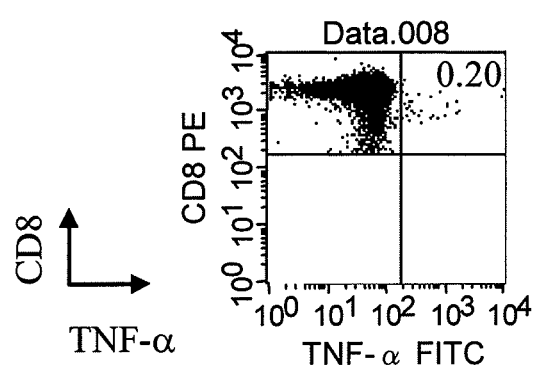
OVA-PIC NP
ε-PL 1/10

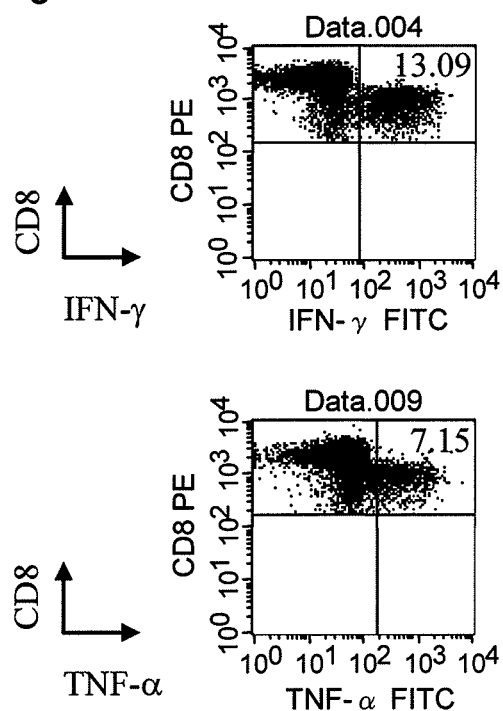

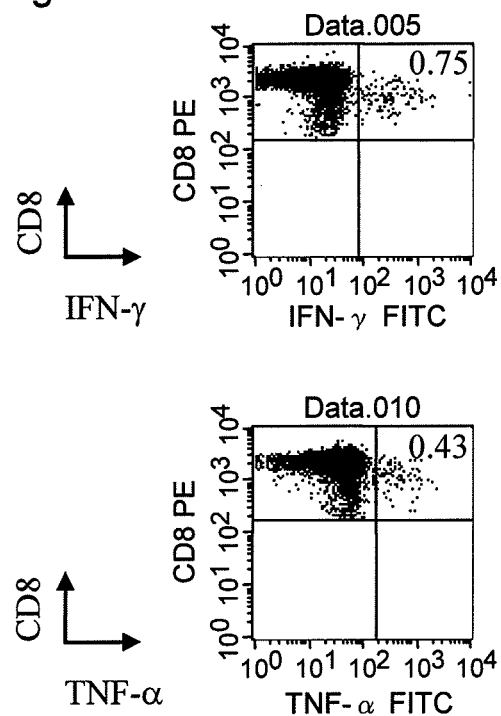

POLYION COMPLEX COMPRISING HYDROPHOBIZED POLYAMINO ACID AND USE OF THE SAME

This application is a U.S. national stage of International Application No. PCT/W2010/055463 filed Mar. 26, 2010.

The present application claims a benefit of the application No. 2009-079712 filed in Japan on Mar. 27, 2009, the contents of which are hereby incorporated by reference.

FIELD OF THE INVENTION

The present invention relates to a field of a drug delivery system (DDS). More specifically, the present invention relates to a polyion complex useful as a carrier or an immunotherapy agent that exhibits a high immunity induction effect, and a polyion complex nanoparticle having a particle shape.

BACKGROUND OF THE INVENTION

A drug delivery system (DDS) for making an effect of drugs to exhibit at the maximum is essential in a pharmaceutical development field, and development of a carrier for delivering the drugs is important. A carrier system utilizing a polymer nano-assembly allows construction of multifunctional polymer devices by a precise molecular design of a polymer chain, and has been anticipated as a DDS carrier application. As a polymer carrier used in this field, micelles, nano-gel particles, nanospheres, nano-capsules, and the like are known, and spontaneous assembly of polymers due to inter- or intra-interaction of the polymer chains has been utilized as driving force for particle formation in preparation of these nano-carriers. Examples of interaction worked in this spontaneous assembly include hydrophobic interaction, electrostatic interaction, hydrogen-bonding, van der Waals force, and the like (Patent Documents 1-13).

In particular, a polyion complex (hereinafter, abbreviated as "PIC") which comprises polymers having opposite charge (cations and anions) and a PIC nanoparticle having a particle shape have an advantage that they can be easily prepared only by mixing two kinds of polymers in an arbitral ratio and, therefore, various PICs and PIC nanoparticles utilizing synthetic or naturally occurring polymers have been reported (for example, Patent Document 14). However, because formation of these PICs and PIC nanoparticles utilizes Coulomb's force as driving force, there has been problems that stability of the nanoparticles is poor against a high salt concentration such as in buffers and pH alteration and, therefore, a use thereof under physiological environments is limited.

[Patent Document 1] Japanese Patent Publication No. 2000-5296A
[Patent Document 2] Japanese Patent Publication No. 2000-126585A
[Patent Document 3] Japanese Patent Publication No. 2001-81237A
[Patent Document 4] Japanese. Patent Publication No. 2001-146556A
[Patent Document 5] Japanese Patent Publication No. 2002-638A
[Patent Document 6] Japanese Patent Publication No. 2004-294231A
[Patent Document 7] Japanese Patent Publication No. 2004-352972A
[Patent Document 8] Japanese Patent Publication No. 2005-8614A
[Patent Document 9] Japanese Patent Publication No. 2006-67889A
[Patent Document 10] Japanese Patent Publication No. H05-84665A
[Patent Document 11] WO 06/25419
[Patent Document 12] WO 06/90924
[Patent Document 13] WO 08/62909
[Patent Document 14] Japanese Patent Publication No. H10-77342A

SUMMARY OF THE INVENTION

On the other hand, a PIC and PIC nanoparticle prepared with a hydrophobized polyamino acid, the polymer is assembled by electrostatic interaction to form a particle, can form a stable structure due to hydrophobic interaction, and can exhibit their function even under physiological environment. In a conventional PIC nanoparticle or polymer micelle, stability in vivo has been achieved by chemically crosslinking a core (interior) and a shell (exterior) after particle formation.

However, these procedures have problems that a structure or function of the PIC and PIC nanoparticle may be easily changed depending upon a cross-linking condition. In addition, taking a use in vivo into consideration, there is a problem that a cross-linking manner of the PIC and PIC nanoparticle is limited in the light of their biodegradability.

Therefore, development of the PIC and PIC nanoparticle exhibiting high stability together with high functionality even in vivo is needed.

Under these circumstances, the inventors studied intensively the PIC and PIC nanoparticle that exhibit high stability even in vivo together with suitable biodegradability and, as the result, found that the PIC and PIC nanoparticle obtainable by mixing a water-soluble polyamino acid having a negative charge, to which a hydrophobic amino acid residue has been introduced (hydrophobized poly(acidic amino acid)), and a polyamino acid having a positive charge (basic polypeptide) satisfies these requirements, and found that a high immunity induction ability is exhibited when an antigen is conjugated to or incorporated into such a PIC nanoparticle to administer into organisms, which resulted in completion of the present invention.

That is, the present invention provides:

[1] A polyion complex (PIC) comprising a hydrophobized poly(acidic amino acid) and a basic polypeptide.

[2] A PIC comprising a hydrophobized poly(acidic amino acid) and a basic polypeptide in a ratio of 20:1 to 1:20 (weight ratio).

[3] The PIC according to [1] or [2], wherein the hydrophobized poly(acidic amino acid) is comprised of a unit (A) represented by a general formula (I):

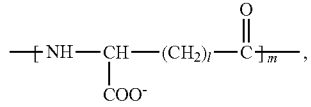

and
a unit (B) represented by a general formula (II):

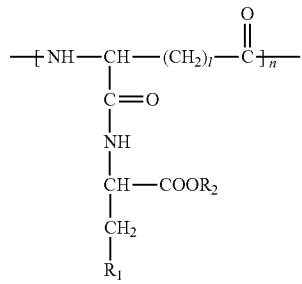

wherein, $R_1$ is a non-substituted or substituted phenyl or indolyl group, $R_2$ is a linear or branched alkyl, alkenyl or alkynyl group having a carbon atom number of 1 to 5; l is an integer of 1 or 2; the sum of m and n is 40 to 40,000, and wherein a molar ratio of the unit (A) and the unit (B) ((m):(n)) is 10:90 to 90:10.

[4] The PIC according to any one of [1] to [3], wherein the basic polypeptide is poly(ε-lysine) having an average molecular weight of $1.0\times10^3$-$1.0\times10^4$.

[5] The PIC according to any one of [1] to [3], wherein the basic polypeptide is protamine.

[6] The PIC according to any one of [1] to [5], wherein the molar ratio ((m):(n)) is 15:85 to 85:15.

[7] The PIC according to any one of [1] to [6], wherein it has a particle shape.

[8] The PIC according to [7], wherein it has an average particle diameter of 0.01 to 1 μm.

[9] A process for preparing a PIC, comprising steps of (1) introducing a hydrophobic amino acid to a poly(acidic amino acid) to prepare a hydrophobized poly(acidic amino acid); and (2) dissolving the hydrophobized poly(acidic amino acid) prepared to a buffer, and it is mixed with a basic polypeptide dissolved in a buffer.

[10] The process according to [9], wherein the hydrophobized poly(acidic amino acid) and the basic polypeptide are mixed in 20:1-1:20 (weight ratio).

[11] The process according to [9] or [10], wherein the basic polypeptide is poly(ε-lysine) having an average molecular weight of $1.0\times10^3$-$1.0\times10^4$.

[12] The process according to [9] or [10], wherein the basic polypeptide is protamine.

[13] The process according to any one of [9] to [12], wherein the poly(acidic amino acid) to which the hydrophobic amino acid has not been introduced in the hydrophobized poly(acidic amino acid) is represented by a general formula (I):

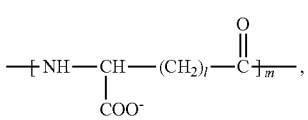

and
the poly(acidic amino acid) to which the hydrophobic amino acid has been introduced is represented by a general formula (II):

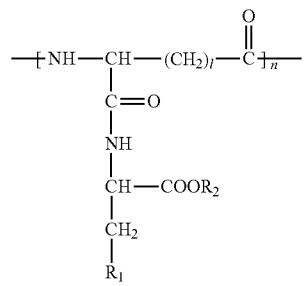

wherein, $R_1$ is a non-substituted or substituted phenyl or indolyl group, $R_2$ is a linear or branched alkyl, alkenyl or alkynyl group having a carbon atom number of 1 to 5; l is an integer of 1 or 2; the sum of m and n is 40 to 40,000, and wherein the molar ratio ((m):(n)) is 15:85 to 85:15.

[14] The process according to any one of [9] to [13], wherein organic solvent is not used.

[15] The process according to any one of [9] to [14], wherein the PIC prepared has a particle shape.

[16] The process according to [15], wherein the PIC prepared has an average particle diameter of 0.01 to 1 μm.

[17] An immunotherapy agent comprising the PIC of [7] or [8] to which an antigen has been conjugated or incorporated and/or which has been mixed with the antigen.

[18] The immunotherapy agent according to [17], that is able to induce humoral immunity and cell-mediated immunity.

[19] The immunotherapy agent according to [17] or [18], wherein the antigen is ovalbumin.

[20] The immunotherapy agent according to [17] or [18], wherein the antigen is influenza hemagglutinin.

[21] A process for preparing an immunotherapy agent comprising conjugating or incorporating an antigen to the PIC of [7] or [8] and/or mixing the antigen with the PIC.

[22] The process for preparing an immunotherapy agent according to [21], wherein the antigen is ovalbumin.

[23] The process for preparing an immunotherapy agent according to [21], wherein the antigen is influenza hemagglutinin.

According to the present invention, a PIC or a PIC nanoparticle that may be easily prepared, and that are finally disappeared in vivo due to its suitable biodegradability while exhibiting high stability in the organisms are provided. In addition, according to the present invention, an immunotherapy agent against infectious diseases, cancers, autoimmune disorders, and the like is provided, comprising the PIC or the PIC nanoparticle to which various antigen proteins or peptides may be easily conjugated or incorporated and/or which may be mixed with various antigen proteins or peptides.

BRIEF DESCRIPTION OF DRAWINGS

FIG. 5A is a diagram showing a cell-mediated immunity activating effect with the ovalbumin-conjugated PIC nanoparticle of the present invention (PBS).

FIG. 7A is a diagram showing a cell-mediated immunity activating effect of the PIC nanoparticle of the present invention, in which a basic polypeptide has been modified (PBS).

FIG. 7B is a diagram showing a cell-mediated immunity activating effect of the PIC nanoparticle of the present invention, in which a basic polypeptide has been modified (PIC nanoparticle with ε-PL, ×1 concentration).

FIG. 7C is a diagram showing a cell-mediated immunity activating effect of the PIC nanoparticle of the present invention, in which a basic polypeptide has been modified (PIC nanoparticle with ε-PL, ×1/10 concentration).

FIG. 7D is a diagram showing a cell-mediated immunity activating effect of the PIC nanoparticle of the present invention, in which a basic polypeptide has been modified (PIC nanoparticle with protamine, ×1 concentration).

FIG. 7E is a diagram showing a cell-mediated immunity activating effect of the PIC nanoparticle of the present invention, in which a basic polypeptide has been modified (PIC nanoparticle with protamine, ×1/10 concentration).

DETAILED DESCRIPTION OF THE PREFERRED EMBODIMENTS

Figure 1:
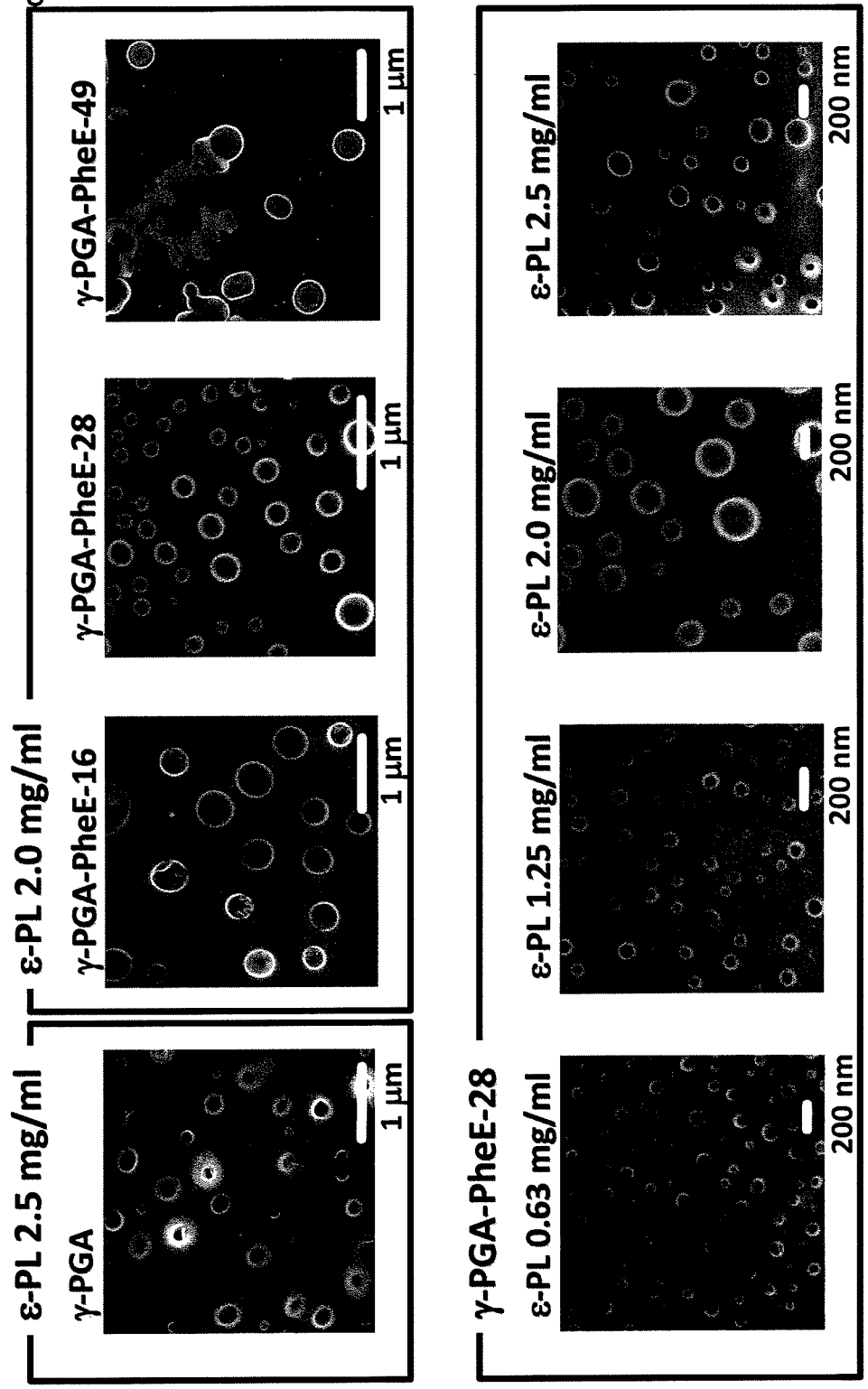
FIG. 1 is a scanning electron micrograph (SEM) of a PIC nanoparticle of the present invention.

In the first aspect, the present invention provides a polyion complex (PIC) comprising a hydrophobized poly(acidic amino acid) and a basic polypeptide.

The hydrophobized poly(acidic amino acid) used in the present invention is usually comprised of a unit (A) represented by a general formula (I):

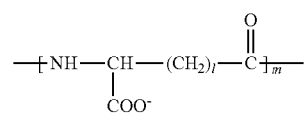

and a unit (B) represented by a general formula (II):

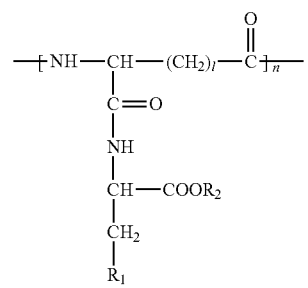

wherein, $R_1$ is a non-substituted or substituted phenyl or indolyl group, $R_2$ is a linear or branched alkyl, alkenyl or alkynyl group having a carbon atom number of 1 to 5; l is an integer of 1 or 2; the sum of m and n is 40 to 40,000, wherein a molar ratio of the unit (A) and the unit (B) ((m):(n)) is 10:90 to 90:10. In addition, in general, the hydrophobized poly(acidic amino acid) used in the present invention may be obtained by partially linking via an amide bond an amino group of an alkyl, alkenyl or alkynyl ester of an aromatic amino acid to a carboxyl group of the poly(acidic amino acid) that is obtainable by polymerization of an acidic amino acid having pKa not more than about 7, preferably not more than about 6, and more preferably not more than about 4. Examples of the acidic amino acid used herein include glutamic acid, aspartic acid or derivatives thereof. The poly(acidic amino acid) may be prepared by polymerization of one kind of the acidic amino acid, or by random copolymerization, alternating copolymerization, periodic copolymerization or block copolymerization of two or more kinds of the acidic amino acid. Preferably, it is poly(γ-glutamic acid) derived from microorganisms in which glutamic acid is solely polymerized. A degree of polymerization of the poly(acidic amino acid) is usually about 40-40,000, preferably about 400-15,000, more preferably about 800-8,000, and most preferably about 1,500-6,000. An average molecular weight of the poly(acidic amino acid) is usually about $5.0×10^3$-$5.0×10^6$, preferably about $5.0×10^4$-$2.0×10^6$, more preferably about $1.0×10^5$-$1.0×10^6$, and most preferably about $2.0×10^5$-$8.0×10^5$. In addition, examples of an aromatic amino acid ester to be liked to the obtained poly(acidic amino acid) include a linear or branched alkyl, alkenyl or alkynyl ester, having a carbon atom number of 1 to 5, of phenylalanine, tyrosine, tryptophan or derivatives thereof, and one or more thereof may be linked to a carboxyl group of the poly(acidic amino acid) via an amide bond. A molar ratio of the unit (A) and the unit (B) constituting the poly(acidic amino acid) ((m):(n)) is usually about 10:90-90:10, preferably about 15:85-85:15, more preferably about 20:80-80:20, still more preferably about 30:70-80:20, and most preferably about 45:55-80:20.

Furthermore, a polymerization method of the acidic amino acid, an esterification method of the aromatic amino acid, an introduction method of the aromatic amino acid ester to the poly(acidic amino acid), a method for controlling a degree of polymerization or an introduction ratio, and the like may be conducted according to methods known in the art per se.

The basic polypeptide used in the present invention may be obtained by polymerization of a basic amino acid having pKa not less than about 7, preferably not less than about 7.5, and more preferably not less than about 8, or as a naturally-occurring polypeptide. Examples of the basic amino acid used herein include lysine, hydroxylysine, arginine, histidine or derivatives thereof, and the basic polypeptide may be obtained by polymerization of one of them, or by random copolymerization, alternating copolymerization, periodic copolymerization or block copolymerization of two or more of them, but preferably it is poly(ε-lysine) derived from microorganisms, in which lysine is solely polymerized. In addition, examples of a naturally-occurring basic polypeptide include protamine. A degree of polymerization of the basic polypeptide is usually about 8-80, preferably 10-70, more preferably about 20-60, and most preferably about 30-50, and an average molecular weight of the basic polypeptide is usually about $1.0\times10^3$-$1.0\times10^4$, preferably about $1.3\times10^3$-$9.0\times10^3$, more preferably about $2.5\times10^3$-$7.5\times10^3$, and most preferably about $3.8\times10^3$-$6.4\times10^3$.

The PIC of the present invention may be easily prepared only by dissolving aforementioned hydrophobized poly(acidic amino acid) and basic polypeptide to pure water, a physiological salt solution or buffer and mixing them. In addition, in a preferable embodiment, the PIC is a PIC nanoparticle having a particle shape, and such a PIC nanoparticle is also included in a scope of the present invention. Examples of the buffer to be used are not particularly limited so long as they are able to homogeneously dissolving aforementioned hydrophobized poly(acidic amino acid) and basic polypeptide without denaturation, but include, for example, phosphate-buffered physiological saline (PBS) having pH of 6-8.5, and the like. The PIC and PIC nanoparticle may be prepared by separately dissolving the hydrophobized poly(acidic amino acid) and the basic polypeptide to same or different buffer, and mixing them at room temperature. A mixing ratio of each solution may be equal. A mixing ratio of the hydrophobized poly(acidic amino acid) and the basic polypeptide (hydrophobized poly(acidic amino acid): basic polypeptide) is usually about 20:1-1:20, preferably about 10:1-1:10, more preferably about 8:1-1:8, most preferably about 6:1-1:6 to about 6:1-1:1, and still most preferably about 6:1-3:1. In addition, in a certain embodiment, the PIC and the PIC nanoparticle of the present invention may be prepared without use of organic solvent.

A particle diameter of the PIC nanoparticle of the present invention is usually about 0.01-1 μm, preferably about 0.02-0.8 μm, more preferably about 0.05-0.6 μm, and most preferably about 0.1-0.4 μm as an average particle diameter. In the case where the particle diameter of the PIC nanoparticle is less than 0.01 μm, an ability as an antigen carrier is lowered, whereas in the case where it is greater than 1 μm, an adjuvant activity is lowered, and hence both cases are unpreferable.

An average particle diameter of the PIC nanoparticle may be controlled by changing a ratio of the hydrophobic amino acid residue in a hydrophobized poly(acidic amino acid) chain and/or a molecular weight and a mixing ratio of the hydrophobized poly(acidic amino acid) and the basic polypeptide. An average particle diameter of a produced PIC nanoparticle may be measured with Dynamic Light Scattering (DLS).

In the second aspect, the present invention provides an immunotherapy agent comprising an antigen-conjugated PIC nanoparticle that is prepared by conjugating or incorporating an antigen to the PIC nanoparticle obtainable by procedures as described above. A carrier and adjuvant of the antigens used in the immunotherapy agent of the present invention is the PIC nanoparticle that may be obtained as described above and that is finally degraded by a degrading enzyme, and metabolized, detoxified or lowered in toxicity. On the other hand, examples of the antigen is not particularly limited, but include, for example, a protein antigen included in foods such as ovalbumin, a malignant tumor antigen, an antigen of a pathogen such as pathogenic virus or bacteria, and the like. Examples of malignant tumor include breast cancer, lung cancer, stomach cancer, colon cancer, liver cancer, ovarian cancer, bladder cancer, leukemia, malignant melanoma, and the like, and examples of pathogen include adult T-cell lymphoma virus, hepatitis virus, human acquired immunodeficiency syndrome (AIDS) virus (HIV), influenza virus, Japanese encephalitis virus, and the like.

Moreover, a releasing ratio and duration of the antigen and a duration until the PIC nanoparticle itself is disappeared in vivo may be controlled by properly modifying a material, a constitution ratio, a molecular weight, an average diameter or other parameters of the PIC nanoparticle. Such a method for preparation of such a PIC nanoparticle and antigen is known in the art. For example, a sustained-release immunotherapy agent may be prepared by controlling a molecular weight or degree of polymerization of the hydrophobized poly(acidic amino acid) and the basic polypeptide that constitute the PIC nanoparticle, a kind and ratio of a hydrophobic group to be introduced, a conjugating or incorporating manner of the antigen, a concentration or portion of the antigen to be introduced, an average particle diameter, diameter distribution or shape of the PIC nanoparticle, and the like. In addition, for example, the PIC nanoparticle may be designed such that the antigen is released in a particular organ or part, by introducing a linking to be degraded with an enzyme located in the particular organ or site to a linking between the PIC nanoparticle and the antigen, or to an inside of the PIC nanoparticle.

The immunotherapy agent of the present invention may comprise the PIC nanoparticle to which the antigen is conjugated or incorporated, and vehicles or carriers and, optionally, other ingredients such as suspending agents, isotonicity adjusting agents and preservatives. The vehicles or carriers are not particularly limited so long as they don't affect adversely on the organisms after administration, but examples thereof include for example an aqueous medium such as water, ethanol and glycerol, and a non-aqueous medium such as oils such as fatty acids and fatty acid esters. In addition, a dosage form of the immunotherapy agent of the present invention may be any form and may be properly selected according to a factor such as a state of subjects and a kind of diseases. For example, a dosage form of the immunotherapy agent may be liquids or solutions, suspensions, emulsions, powders, granules, tablets, or capsules. Alternatively, a lyophilized immunotherapy agent may be dissolved or suspended in proper vehicles or carriers prior to use.

Moreover, in the third aspect, the present invention provides immunotherapy agent comprising a mixture of the antigen and the PIC nanoparticle. In this aspect, the antigen and the PIC nanoparticle as well as other ingredients and the dosage forms are the same as those of aforementioned immunotherapy agent comprising an antigen-conjugated PIC nanoparticle, except that the antigen is used by mixing with the PIC nanoparticle instead of being conjugated to or incorporated into the PIC nanoparticle.

An administration manner, route or frequency of the immunotherapy agent of the present invention is not particularly limited, and it may be properly selected according to the factors such as dosage forms, a state of the subjects and a kind of the diseases. For example, the immunotherapy agent of the present invention may be parenterally administered such as by an injection or infusion solution or may be orally administered.

As stated above, the immunotherapy agent of the present invention may be administered to a subject in order for prophylaxis and treatment of various diseases. Hence, in another aspect, the present invention also provides a use of a PIC nanoparticle as an immunotherapy agent and a method for using a PIC nanoparticle for manufacturing an immunotherapy agent. In addition, in another aspect, the present invention provides a method for treatment or prophylaxis of a disease in subjects, comprising administering an immunotherapy agent to the subjects, which comprises a PIC nanoparticle to which the antigen is conjugated or incorporated.

Moreover, in the forth aspect, the present invention provides a method for preparation of the aforementioned PIC and PIC nanoparticle.

The method for preparation of the PIC and PIC nanoparticle of the present invention comprises a preparation step of a water-soluble hydrophobized poly(acidic amino acid) and a mixing step of an aqueous solution of the hydrophobized poly(acidic amino acid) and an aqueous solution of a basic polypeptide. Preparation of the hydrophobized poly(acidic amino acid) may be conducted by linking an amino group of an aromatic amino acid ester to a carboxyl group of a poly (acidic amino acid) via an amide bond with a dehydrocondensing agent such as 1-ethyl-3-(3-dimethylaminopropyl) carbodiimide (WSC) and 1-cyclohexyl-3-[2-(4-methylmorpholinyl)ethyl]carbodiimide-p-toluenesulfonate, and an introduction ratio of the hydrophobic amino acid to the poly(acidic amino acid) may be modified by properly changing a reaction condition such as a concentration of the dehydrocondensing agent and the aromatic amino acid ester and a reaction time.

Although the present invention will be illustrated in more detail and specifically by way of following examples, but the present invention is not limited thereto. In addition, in the examples, poly(γ-glutamic acid) is abbreviated as γ-PGA, and poly(ε-lysine) is abbreviated as ε-PL.

EXAMPLES

Preparation Example 1

Preparation of Hydrophobized Polyamino Acid

In 100 ml of a 50 mM aqueous solution of sodium hydrogen carbonate, 607 mg of γ-PGA (Meiji Co., Ltd., molecular weight $3.8 \times 10^5$, pKa=2.3) derived from a microorganism (*Bacillus subtilis*) was uniformly dissolved. To the solution, 225 to 901 mg of 1-ethyl-3-(3-dimethylaminopropyl)carbodiimide hydrochloride (WSC) and 1080 mg of L-phenylalanine ethyl ester (PheE) were added, and the resulting mixture was reacted on ice for 1 hour, and then at room temperature for 24 hours. After the reaction, the resulting solution was dialyzed against water using a dialysis membrane (molecular weight cut off: 50,000) for 3 days, and then the resulting solution was lyophilized. The obtained lyophilized substance was added to 100 ml of ethanol, and the resulting mixture was stirred overnight. The resulting solution was centrifuged (1,500×g, 20 minutes), and the precipitate was dried under reduced pressure to obtain hydrophobized γ-PGA. The introduction amount of PheE into γ-PGA was adjusted by changing the concentration of WSC. When the PheE introduction ratio of the hydrophobized γ-PGA prepared in the manner described above was measured by $^1$H-NMR, the PheE introduction ratio was found to be 16%, 28%, 36% and 49% (hereinafter abbreviated as γ-PGA-PheE-16, -28, -36 and -49, respectively).

Preparation Example 2

Preparation of Polyion Complex (PIC) Nanoparticle

In PBS (pH 7.4) at 25° C., the various hydrophobized γ-PGA prepared as described above (γ-PGA-PheE-16, -28 and -49) or unmodified γ-PGA (Meiji Co., Ltd., molecular weight: $3.8 \times 10^5$, pKa=2.3) and ε-PL (Chisso Corporation, molecular weight: $4.7 \times 10^3$) derived from a microorganism (*Streptomyces albulus* 346) were separately dissolved at final concentrations of 10 mg/ml and 0 to 5 mg/ml, respectively, and these were equivalently mixed. The average particle diameter and particle diameter distribution immediately after mixing were measured by the dynamic light scattering method (instrument name, Zetasizer Nano ZS, Malvern Instruments Ltd.), and the state of particles was observed by the scanning electron microscope. The results are shown in Table 1 and FIG. 1.

TABLE 1

| Hydrophobized poly(acidic amino acid)[a] | Concentrations of ε-PL (mg/mL) | | | | | |
|---|---|---|---|---|---|---|
| | 0 | 0.625 | 1.25 | 2.0 | 2.5 | 5 |
| | Particle diameter of PIC nanoparticle (nm, average particle diameter ± SE) | | | | | |
| γ-PGA | 14.5 ± 1.9 | 10.9 ± 0.3 | 10.7 ± 0.7 | 15.6 ± 0.7 | 535 ± 19 | 931 ± 172 |
| γ-PGA-PheE-16 | 16.9 ± 3.1 | 12.3 ± 1.0 | 13.9 ± 2.7 | 805 ± 5.1 | 1667 ± 272 | —[b] |
| γ-PGA-PheE-28 | 12.5 ± 0.4 | 225 ± 13 | 231 ± 13 | 337 ± 45 | 362 ± 9.2 | — |
| γ-PGA-PheE-49 | 16.6 ± 1.3 | 134 ± 8.0 | 199 ± 6.1 | 255 ± 58 | — | — |

[a]γ-PGA and γ-PGA-PheE were dissolved in PBS (10 mg/mL) and the solutions were added to the ε-PL solution in an equivalent amount.
[b]Not measured.

As is obvious from Table 1 and FIG. 1, formation of nanoparticles was found immediately after mixing. A tendency where, as a concentration of ε-PL increased, the particle diameter formed increased was found, and the change in the introduction ratio of a hydrophobic group into a hydrophobized poly amino acid also affected the particle diameter depending on combinations with an ε-PL concentration. That is, the particle diameter of PIC nanoparticles of the present invention was shown to be able to control by changing the introduction ratio of a hydrophobic group into a hydrophobized poly(acidic amino acid), and the mixing ratio of a hydrophobized poly(acidic amino acid) and a basic polypeptide.

Example 1

Stability of PIC Nanoparticle

Next, stability of PIC nanoparticles formed as described above was measured. γ-PGA-PheE-16, -28 or -49 (10 mg/mL) to which hydrophobic groups were introduced at various ratios, and ε-PL (2 mg/mL) were separately dissolved in 1 ml of PBS (pH 7.4), and these solutions were equivalently mixed, and then the resulting solutions were allowed to stand at 4° C. and the average particle diameter was measured with time by the dynamic light scattering method (instrument name, Zetasizer Nano ZS, Malvern Instruments Ltd.). The results are shown in FIG. 2.

Figure 2:
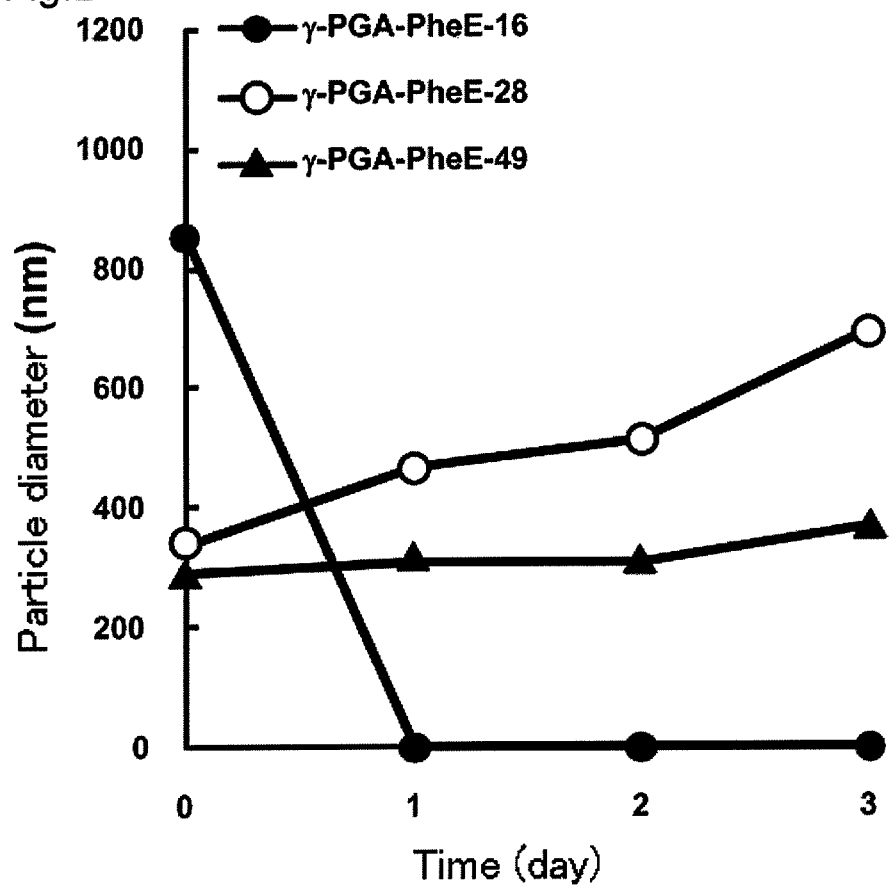
FIG. 2 is a graph showing time-dependent stability of the PIC nanoparticle of the present invention.

As is obvious from FIG. 2, when hydrophobized poly(acidic amino acid) and a basic polypeptide were mixed at a particular ratio, and when γ-PGA-PheE-16 was used, disruption and agglutination of particles were found after 1 day, and a monodispersed peak was not found by the dynamic light scattering method. On the other hand, when γ-PGA-PheE-28 was used, the particle diameter increased by swelling of particles, but monodispersion was maintained over 3 days after preparation. Also, when γ-PGF-PheE-49 was used, high stability was shown, and a large change in the particle diameter was not found over 3 days after preparation. This high stability was due to formation of hydrophobic domains by the PheE groups in the inside of the particles.

Example 2

Immunity Induction Effect of Antigen-Conjugated PIC Nanoparticle

Preparation of Antigen-Conjugated PIC Nanoparticle

The PBS solutions of 10 mg/ml of γ-PGA-PheE-36, 4 mg/ml of ε-PL, and 2 mg/ml of ovalbumin (OVA) were prepared. First, each of 250 μl of ε-PL and OVA solutions were mixed in equal amounts to prepare the ε-PL+OVA mixed solution (2 mg/ml of ε-PL+1 mg/ml of OVA in PBS, 500 μl). To this solution, 500 μl of the γ-PGA-PheE-36 solution was added and mixed to prepare OVA-conjugated PIC nanoparticles (OVA-PIC NP). The particle diameter of OVA-PIC NP was 213 nm.

Immunity Induction Effect of PIC Nanoparticle

Next, the immunity induction effect of OVA-conjugated PIC nanoparticles (OVA-PIC NP) prepared in the manner described above was evaluated. C57BL/6 mice aged 6 weeks were immunized subcutaneously twice at 1-week intervals with PBS alone, OVA dissolved in PBS alone (0.5 mg/ml), complete Freund's adjuvant (CFA) to which 0.5 mg/ml of OVA were added alone, or OVA-PIC NP (OVA: 0.5 mg/ml, γ-PGA-PheE-36: 5 mg/ml, ε-PL: 1 mg/ml) alone (inoculation amount of 0.2 mL each). At 1 week after final immunization, spleens were removed from the mice, and the existence of $CD8^+$ T cells specific to OVA in the spleen cells (cell-mediated immunity) was analyzed by flow cytometry after dyed with H-2 kb/SIINFEKL (OVA 257-264 peptide)-Pro5 MHC Pentamer (ProImmune Inc.) and FITC labeled anti-$CD8^+$ antibody. The results are shown in FIG. 3.

Figure 3:
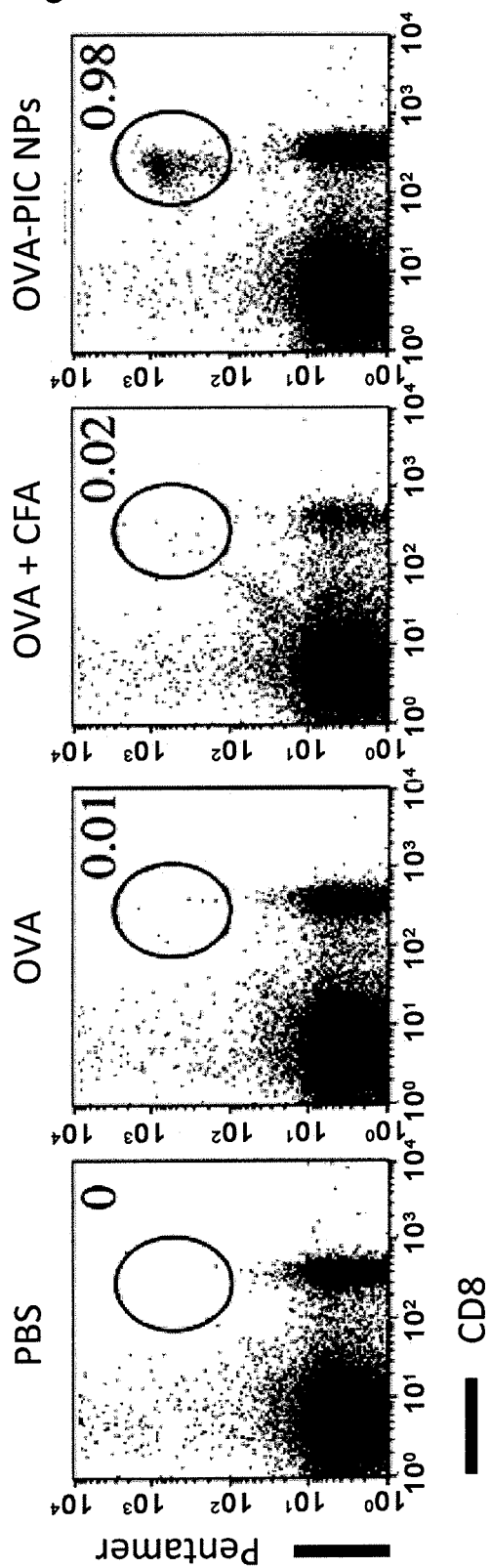
FIG. 3 is a diagram showing a cell-mediated immunity induction effect of an ovalbumin-conjugated PIC nanoparticle of the present invention.

As is obvious from FIG. 3, in the animal groups immunized with PBS alone, OVA alone and OVA+CFA, the induction of cell-mediated immunity was hardly found, whereas in the animal group immunized with OVA-PIC NP, an extremely high immunity induction effect was confirmed.

From the above results, it is believed that OVA-PIC NP exhibited high stability in vivo, and showed a superior immunity induction effect by efficiently delivering the antigens to antigen-presenting cells.

Example 3

In addition, the immunity induction effect of OVA-PIC NP was evaluated according to the method of Example 2 except that newly prepared γ-PGA-PheE-40 was used in place of γ-PGA-PheE-36 and aluminum hydroxide (Alum) was used in place of complete Freund's adjuvant (CFA) in Example 2. The results are shown in FIG. 4.

Figure 4:
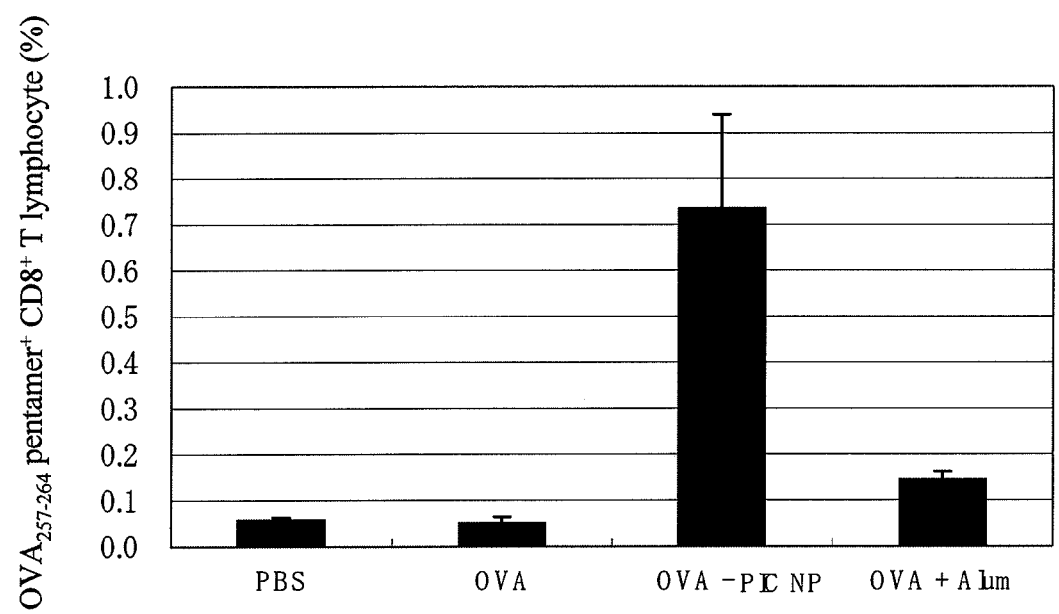
FIG. 4 is a graph showing a cell-mediated immunity induction effect of the ovalbumin-conjugated PIC nanoparticle of the present invention.
Figure 5B:
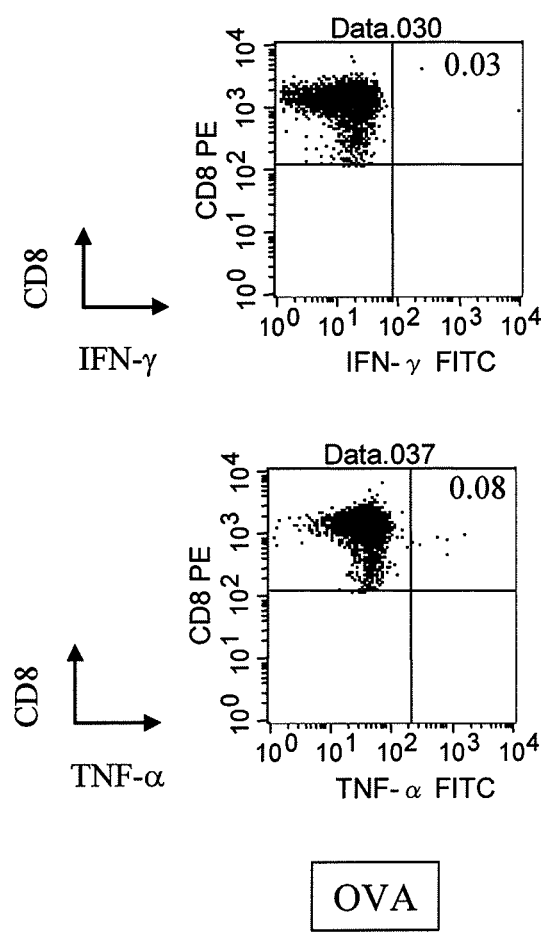
FIG. 5B is a diagram showing a cell-mediated immunity activating effect with the ovalbumin-conjugated PIC nanoparticle of the present invention (ovalbumin).
Figure 5C:
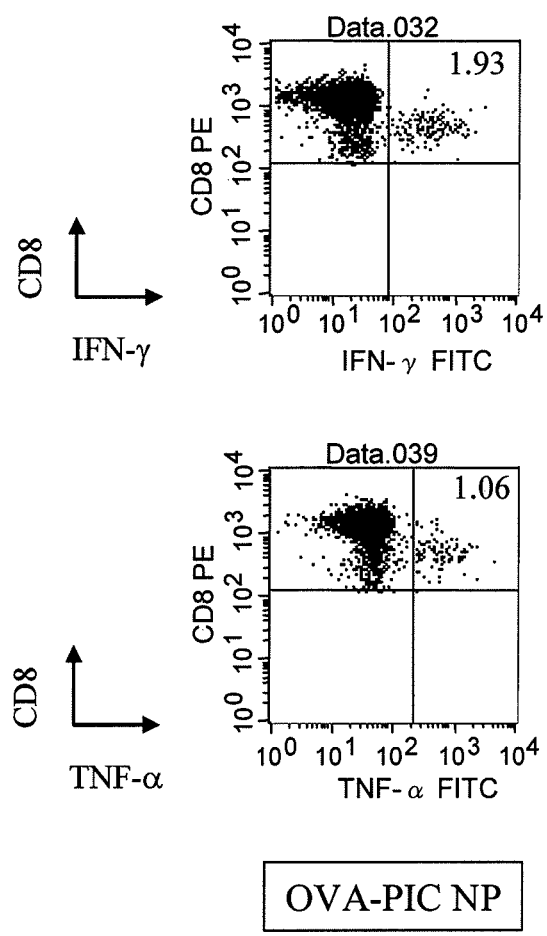
FIG. 5C is a diagram showing a cell-mediated immunity activating effect with the ovalbumin-conjugated PIC nanoparticle of the present invention (ovalbumin-conjugated PIC nanoparticle).
Figure 5D:
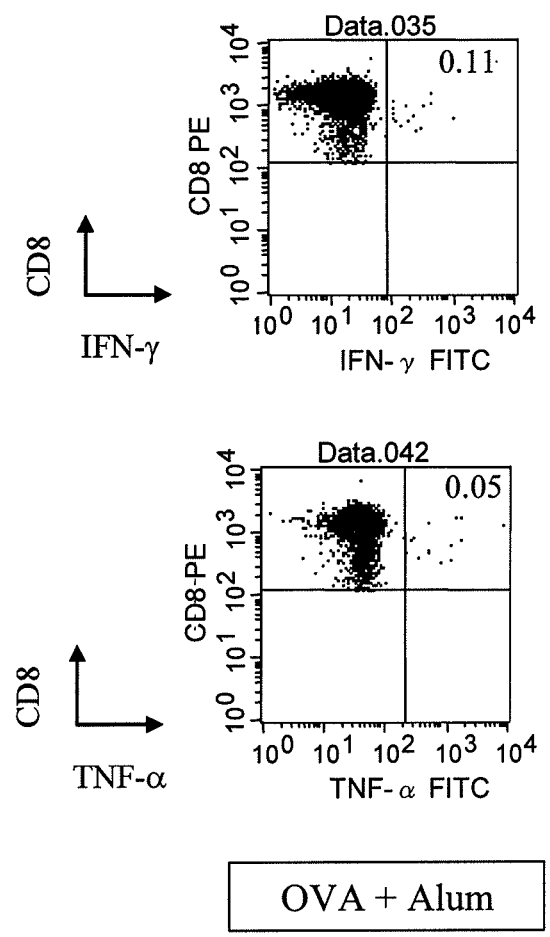
FIG. 5D is a diagram showing a cell-mediated immunity activating effect with the ovalbumin-conjugated PIC nanoparticle of the present invention (ovalbumin and aluminum hydroxide).

As is obvious from FIG. 4, in the animal groups immunized with PBS alone, OVA alone and OVA+Alum, induction of cell-mediated immunity was hardly found, whereas in the animal group immunized with OVA-PIC NP, an extremely high immunity induction effect was confirmed.

The results of Example 2 and Example 3 revealed that OVA-PIC NP exhibited high stability in vivo, and exhibited a superior cell-mediated immunity-induction effect to that of conventional adjuvant by efficiently delivering the antigens to the antigen-presenting cells.

Example 4

Next, the spleen cells removed from mouse spleens in Example 2 were stimulated with a cytotoxic T lymphocyte epitope peptide (10 μg/ml), and the number of interferon (IFN)-γ and tumor necrosis factor (TNF)-α producing cells in all $CD8^+$ T cells was measured by the ELISPOT method. The results are shown in FIGS. 5A-D.

As is obvious from FIGS. 5A-D, in the animal groups immunized with PBS alone, OVA alone and OVA+Alum, IFN-γ and TNF-α-producing cells were hardly found, whereas in the animal group immunized with OVA-PIC NP, cytokine-producing cells were found at a high ratio (the number in the right upper of each chart represents the ratio of cytokine-producing cells in all $CD8^+$ T cells).

The results revealed that antigen-specific $CD8^+$ T cells shown in Example 3 were actually activated by PIC NP of the present invention, and revealed that PIC NP exhibited a superior cell-mediated immunity activating effect over that of conventional adjuvant.

Example 5

Preparation of Antigen-Conjugated PIC Nanoparticle

The PBS solutions of 10 mg/ml of γ-PGA-PheE-40, 4 mg/ml of ε-PL or protamine, and 2 mg/ml of ovalbumin (OVA) were prepared. Each 250 μl of the ε-PL or protamine solution and the OVA solution was mixed in equal amounts to prepare an ε-PL or protamine+OVA mixed solution (2 mg/ml of ε-PL or protamine+2 mg/ml of OVA in PBS, 500 μl). To the solution, 500 μl of the γ-PGA-PheE-40-PBS solution was added and mixed to prepare OVA-conjugated PIC nanoparticles (OVA-PIC NP). The particle diameter of OVA-PIC NP ε-PL and OVA-PIC NP protamine was 220 and 187 nm, respectively. Also, diluted solutions were adjusted with PBS.

Immunity Induction Effect of PIC Nanoparticle

Next, a cell-mediated immunity induction effect of OVA-conjugated PIC nanoparticles (OVA-PIC NP) prepared in the manner described above was evaluated. C57BL/6 mice aged 6 weeks were immunized subcutaneously twice at 1-week intervals with 100 μl of PBS alone, or 200 μl of OVA-PIC NP (OVA: 0.5 mg/ma, γ-PGA-PheE-40: 5 mg/ml, ε-PL or protamine: 1 mg/ml), or 100 µl of OVA-PIC NP (OVA: 0.1 mg/ml, γ-PGA-PheE-40:1 mg/ml, ε-PL or protamine: 0.2 mg/ml). At 1 week after final immunization, spleens were removed from the mice, and the existence of CD8$^+$ T cells specific to OVA (cell-mediated immunity) in spleen cells was analyzed by flow cytometry after dyed with H-2 kb/SIINFEKL (OVA 257-264 peptide)-Pro5 MHC Pentamer (ProImmune Inc.) and FITC labeled anti-CD8$^+$ T antibody. The results are shown in FIG. 6.

Figure 6:
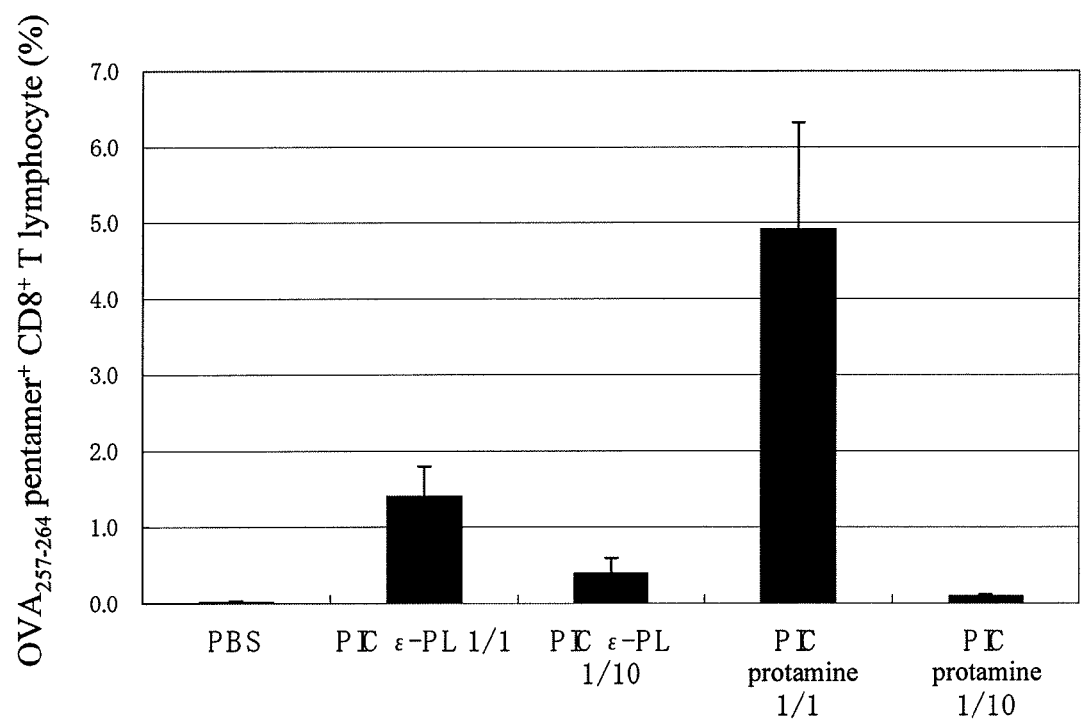
FIG. 6 is a graph showing a cell-mediated immunity induction effect of the PIC nanoparticle of the present invention, in which a basic polypeptide has been modified.

As is obvious from FIG. 6, in the animal group immunized with PBS alone, induction of cell-mediated immunity was hardly found, whereas in the animal group immunized with OVA-PIC NP prepared with protamine, an extremely high cell-mediated immunity-induction effect over that of the animal group immunized with OVA-PIC NP prepared with ε-PL was confirmed.

These results revealed that OVA-PIC NP prepared with protamine as well as ε-PL exhibited high stability in vivo, and exhibited a superior cell-mediated immunity induction effect by efficiently delivering the antigens to the antigen-presenting cells.

Example 6

Next, the spleen cells removed from mouse spleen in Example 5 were stimulated with the cytotoxic T lymphocyte epitope peptide (10 µg/ml), and the number of interferon (IFN)-γ- and tumor necrosis factor (TNF)-α-producing cells in all cells was measured by the ELISPOT method. The results are shown in FIGS. 7A-E.

As is obvious from FIGS. 7A-E, in the animal group immunized with PBS alone, IFN-γ- and TNF-α-producing cells were hardly found, whereas in the animal group immunized with OVA-PIC NP prepared with protamine, an extremely high cell-mediated immunity activating effect over that of the animal group immunized with OVA-PIC NP prepared with ε-PL was confirmed (the number in the right upper of each chart represents the ratio of cytokine-producing cells in all CD8$^+$ T cells).

The results revealed that PIC NP prepared with protamine of the present invention as well as that prepared with ε-PL could actually activate antigen-specific CD8$^+$ T cells and exhibited a superior cell-mediated immunity activating effect over that of conventional adjuvant.

Example 7

In addition, serums were removed from the mice in Example 5, and the antibody titer of the produced OVA-specific immunoglobulin IgG was measured by the ELISA method. The results are shown in FIG. 8.

Figure 8:
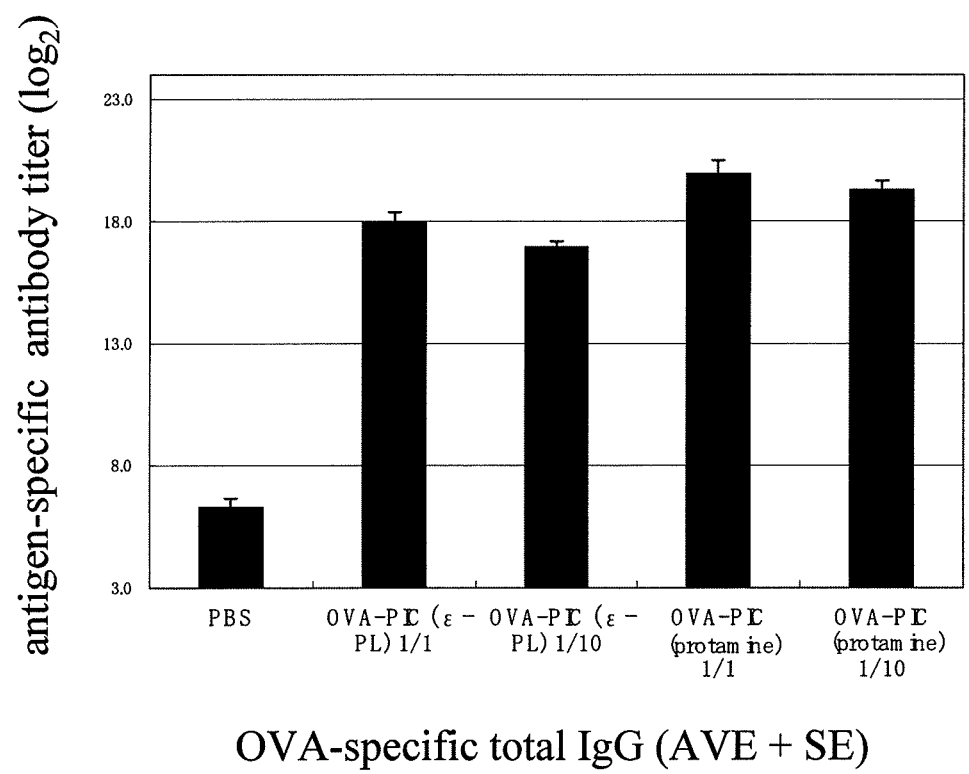
FIG. 8 is a graph showing a humoral immunity activating effect by the ovalbumin-conjugated PIC nanoparticle of the present invention.

As is obvious from FIG. 8, in the animal group immunized with PBS alone, only low antigen specific antibody titers were found, whereas in the animal groups immunized with PIC NP of the present invention prepared with ε-PL or protamine, high OVA specific IgG antibody titers were found.

The results revealed that in the animal immunized with PIC NP of the present invention, an antigen-specific antibody was generated with high antibody titers, and revealed that PIC NP exhibited the effect of inducing humoral immunity as well as cell-mediated immunity.

Example 8

Induction of Humoral and Cell-Mediated Immunity Against Influenza Antigen

Sperm eggs (fertilized eggs) were placed in an incubator at temperature of 38-39° C. for approximately 11 days, and development of embryos was confirmed, and then a hole to pass a needle was punctured in an egg shell. Influenza viruses (A/Hiroshima strain (H3N2), A/Solomon islands strain (H1N1) and B/Malaysia strain), which were vaccine production strains, were directly injected to allantoic fluids through the hole, followed by covering the hole, and the eggs were then placed in the incubator again, and stored at temperature of 32-36° C. for approximately 3 days. After that, the virus inoculated eggs were put in a refrigerator overnight, and egg shells were removed, and then the allantoic fluids were aseptically recovered. After impurities such as blood in the recovered fluids were removed, virus particles were purified and concentrated by sucrose density-gradient centrifugation using a zonal centrifuge. The influenza virus suspensions were treated with ether and then formalin was added thereto.

The amount of influenza HA antigens in three strains prepared as described above was measured according to the Single Radial Immunodiffusion test among Potency tests described in Influenza HA Vaccine of Minimum Requirements for Biological Products (Ministry of Health, Labour and Welfare), and influenza HA antigen fluids were prepared.

The content of HA antigens of three strains of prepared influenza HA antigens were A/Hiroshima strain, 502.4 µg/ml, A/Solomon islands strain, 1262.5 µg/ml, and B/Malaysia strain, 611.0 µg/ml.

Method for Immunizing Mice

Mice aged 4 weeks (BALB/c, male) were divided into the following 6 groups (4 mice in each group), and mice were immunized subcutaneously with the following component(s) in each group, alone or in combination, at 100 µl per a mouse.

Group 1: PBS-administered group
Group 2: HA antigen alone immunized group (each strain 0.3 µg/mouse)
Group 3: HA antigen (each strain 0.3 µg/mouse)+Imject Alum (100 µg/mouse, PIERCE Biotechnology Inc.) immunized group
Group 4: HA antigen (each strain 0.3 µg/mouse)+γ-PGA NP (100 µg/mouse) immunized group
Group 5: HA antigen (each strain 0.3 µg/mouse)+PIC NP (100 µg/mouse) immunized group
Group 6: HA antigen (each strain 0.3 µg/mouse)+Freund's adjuvant (GERBU Biotechnik GmbH, 50 µl/mouse) immunized group With regard to the Freund's adjuvant, complete Freund's adjuvants were used for the first immunization, and incomplete adjuvants were used for the second immunization.

Immunization was performed twice at 1 week intervals, and the blood was collected at 1 week after second immunization, and the IgG and HI antibody titers in the blood were evaluated. The results of A/Hiroshima strain, A/Solomon Islands strain and B/Malaysia strain are shown in FIGS. 9 to 11, respectively.

Figure 9:
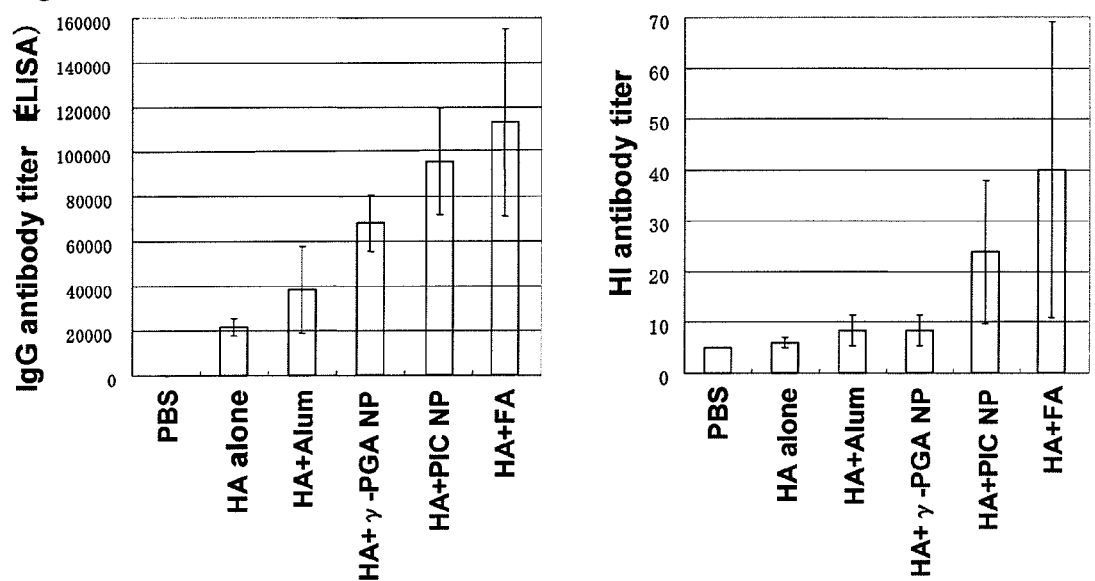
FIG. 9 is a graph showing an increased antibody titer effect against influenza (A/Hiroshima strain) hemagglutinin (HA) by the PIC nanoparticle of the present invention.
Figure 10:
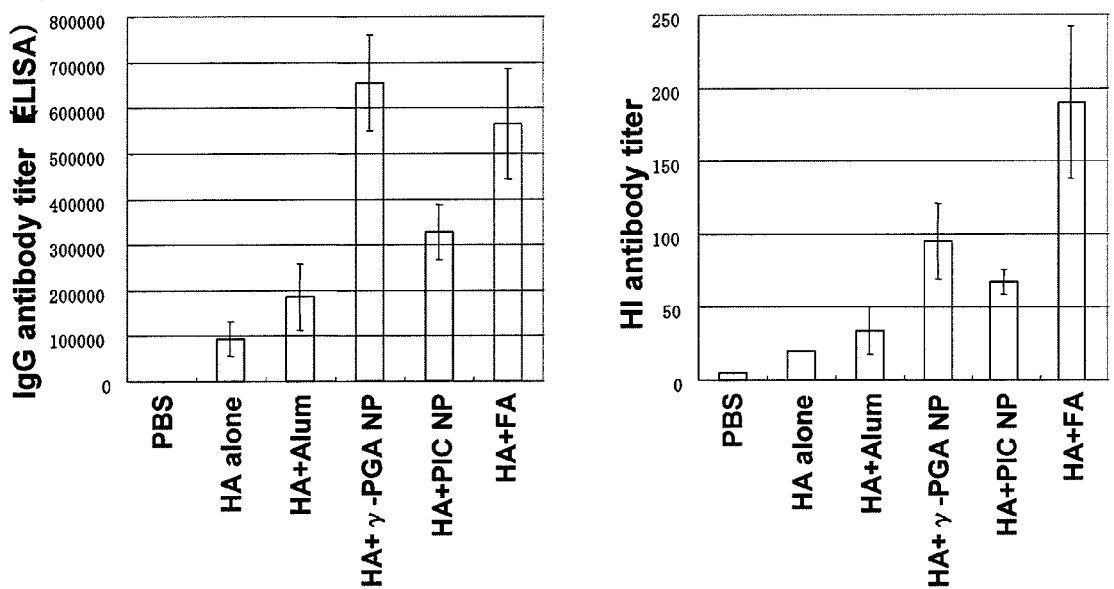
FIG. 10 is a graph showing an increased antibody titer effect against influenza (A/Solomon strain) hemagglutinin (HA) by the PIC nanoparticle of the present invention.
Figure 11:
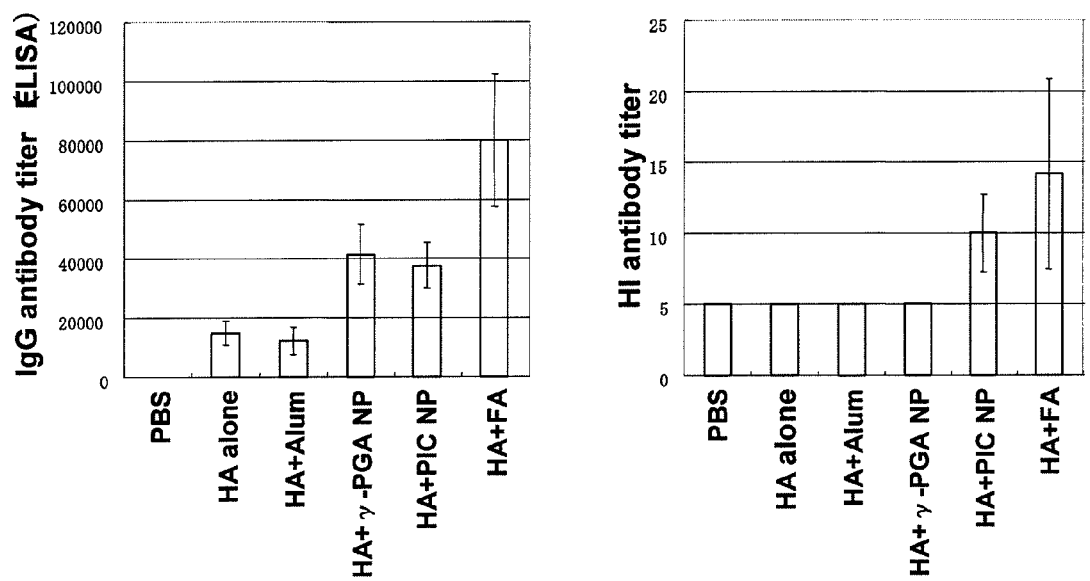
FIG. 11 is a graph showing an increased antibody titer effect against influenza (B/Malaysian strain) hemagglutinin (HA) by the PIC nanoparticle of the present invention.

As is obvious from FIGS. 9 to 11, it was confirmed that PIC NP had an adjuvant activity to all HA antigens of different virus strains, which was the same or more than that of Alum, as the results of the above experiment using ovalbumin (OVA) as an antigen.

The results revealed that in the animal immunized with PIC NP of the present invention, the antigen-specific antibodies with high antibody titers were produced, and revealed that PIC NP had a humoral immunity induction activity to the influenza antigen.

In addition, the spleen cells collected from the mice at 1 week after the second immunization were seeded into wells at a density of 5×10$^5$ cells/100 µl/well, and using ELISpotPLUS for Mouse Interferon-γ kit (Mabtech AB), PBS, the influenza HA antigen (a mixture of 3 strains, A/HI, A/SI and B/MA), and ovalbumin (OVA, Sigma-Aldrich, A2512-250MG, Grade IV) were added at a concentration of 30 ng/ml, and then incubated for approximately 38 hours according to the kit protocol, followed by measuring the number of IFN-γ-producing cells in the spleen cells (each stimulatory antigen of each individual was evaluated using the average of 3 wells). The results are shown in FIG. 12.

Figure 12:
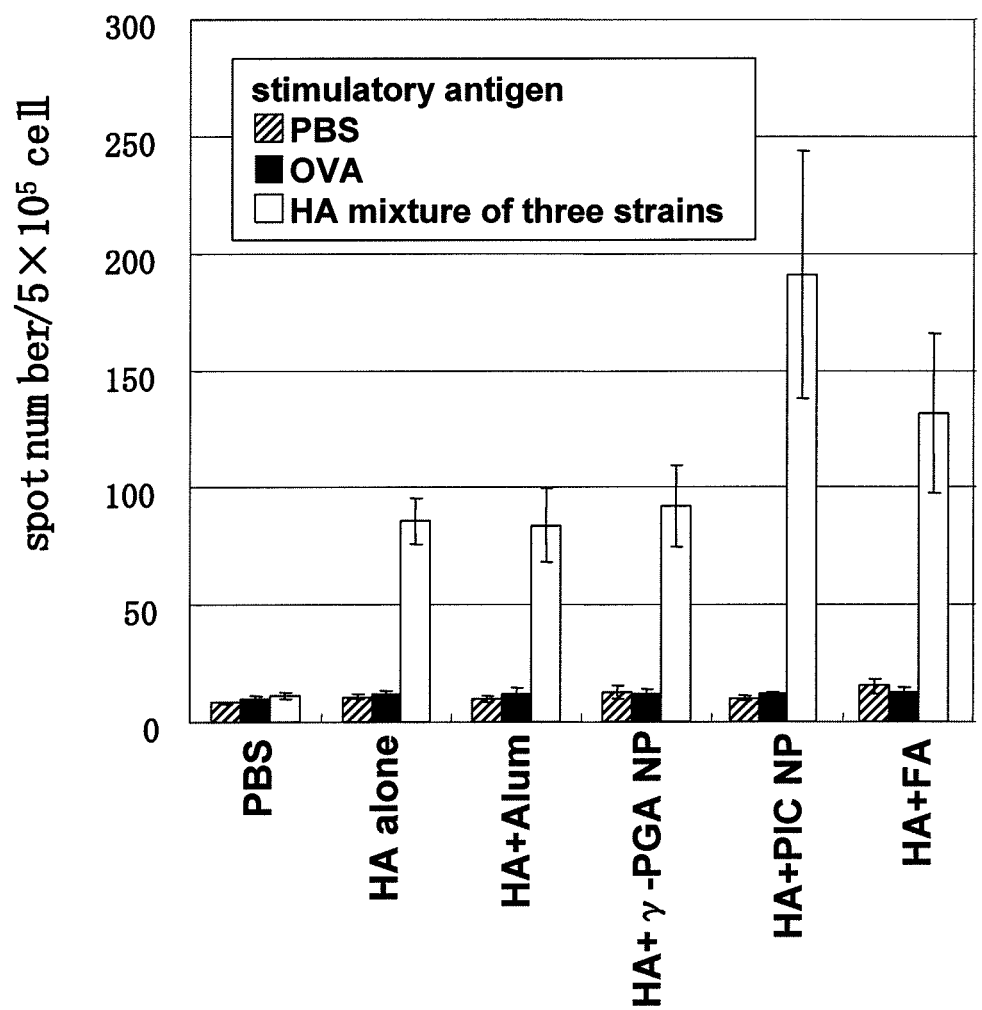
FIG. 12 is a graph showing a cell-mediated immunity activating effect of a mixture of various influenza strain hemagglutinins (HAs) by the PIC nanoparticle of the present invention.

As is obvious from FIG. 12, γ-PGA NP was shown not to be able to induce high cell-mediated immunity. On the other hand, PIC NP was shown to have the cell-mediated immunity activating effect, which was the same or more than that of Freund's adjuvant.

These results revealed that PIC NP of the present invention also exhibited a high immunity-induction effect and activating effect against the influenza HA antigen, and it was shown that a polyion complex and a polyion complex nanoparticle of the present invention are useful as a carrier or an immunotherapy agent.

INDUSTRIAL APPLICABILITY

A polyion complex and a polyion complex nanoparticle of the present invention exhibit an effect enhancing both of cell-mediated immunity and humoral immunity in vivo against various antigens, and are applicable as an immunological adjuvant in a medical or pharmaceutical field.

What is claimed is:

1. A polyion complex (PIC) comprising a hydrophobized poly(acidic amino acid) and a basic polypeptide, wherein the hydrophobized poly(acidic amino acid) is comprised of a unit (A) represented by a general formula (I):

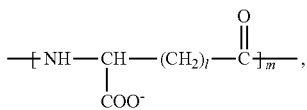

and
a unit (B) represented by a general formula (II):

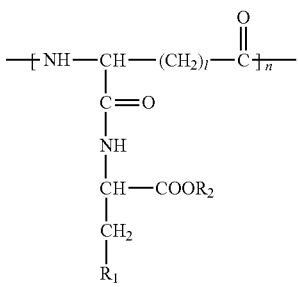

wherein, $R_1$ is a non-substituted or substituted phenyl or indolyl group,
$R_2$ is a linear or branched alkyl, alkenyl or alkynyl group having a carbon atom number of 1 to 5; l is an integer of 1 or 2; the sum of m and n is 40 to 40,000, and wherein a molar ratio of the unit (A) and the unit (B) ((m):(n)) is 10:90 to 90:10.

2. The PIC according to claim 1, comprising a hydrophobized poly(acidic amino acid) and a basic polypeptide in a ratio of 20:1 to 1:20 (weight ratio).

3. The PIC according to claim 1, wherein the basic polypeptide is poly(ε-lysine) having an average molecular weight of $1.0 \times 10^3$-$1.0 \times 10^4$.

4. The PIC according to claim 1, wherein the basic polypeptide is protamine.

5. The PIC according to claim 1, wherein the molar ratio ((m):(n)) is 15:85 to 85:15.

6. The PIC according to claim 1, wherein it has a particle shape.

7. The PIC according to claim 6, wherein it has an average particle diameter of 0.01 to 1 μm.

8. The process for preparing a PIC, comprising steps of
(1) introducing a hydrophobic amino acid to a poly(acidic amino acid) to prepare a hydrophobized poly(acidic amino acid) comprised of a unit (A) represented by a general formula (I):

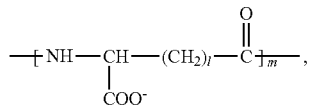

and
a unit (B) represented by a general formula (II):

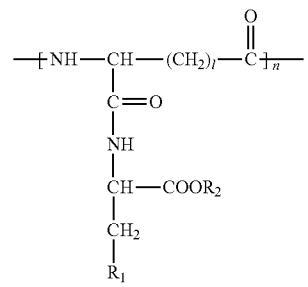

wherein, $R_1$ is a non-substituted or substituted phenyl or indolyl group,
$R_2$ is a linear or branched alkyl, alkenyl or alkynyl group having a carbon atom number of 1 to 5; l is an integer of 1 or 2; the sum of m and n is 40 to 40,000, and wherein a molar ratio of the unit (A) and the unit (B) ((m):(n)) is 10:90 to 90:10; and
(2) dissolving the hydrophobized poly(acidic amino acid) prepared to a buffer, and it is mixed with a basic polypeptide dissolved in a buffer.

9. The process according to claim 8, wherein the hydrophobized poly(acidic amino acid) and the basis polypeptide are mixed in 20:1-1:20 (weight ratio).

10. The process according to claim 8, wherein the basic polypeptide is poly(ε-lysine) having an average molecular weight of $1.0 \times 10^3$-$1.0 \times 10^4$.

11. The process according to claim 8, wherein the basic polypeptide is protamine.

12. The process according to claim 8, wherein organic solvent is not used.

13. The process according to claim 8, wherein the PIC prepared has a particle shape.

14. The process according to claim 13, wherein the PIC prepared has an average particle diameter of 0.01 to 1 μm.

15. An immunotherapy agent comprising the PIC of claim 6 to which an antigen has been conjugated or incorporated and/or the PIC mixed with the antigen.

16. The immunotherapy agent according to claim 15, that is able to induce humoral immunity and cell-mediated immunity.

17. The immunotherapy agent according to claim 15, wherein the antigen is ovalbumin.

18. The immunotherapy agent according to claim 15, wherein the antigen is influenza hemagglutinin.

19. A process for preparing an immunotherapy agent comprising conjugating or incorporating an antigen to the PIC of claim 6 and/or mixing the antigen with the PIC.

20. The process for preparing an immunotherapy agent according to claim 19, wherein the antigen is ovalbumin.

21. The process for preparing an immunotherapy agent according to claim 19, wherein the antigen is influenza hemagglutinin.

* * * * *